United States Patent
Sussman (10) Patent No.: US 12,208,035 B2
(45) Date of Patent: Jan. 28, 2025

(54) APPARATUS AND SYSTEM FOR A DISPOSABLE TORQUE LIMITING TIP WRENCH

(71) Applicant: Johnson & Johnson Surgical Vision, Inc., Irvine, CA (US)

(72) Inventor: Matthew A. Sussman, Laguna Niguel, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 237 days.

(21) Appl. No.: 16/860,011

(22) Filed: Apr. 27, 2020

(65) Prior Publication Data
US 2021/0330495 A1    Oct. 28, 2021

(51) Int. Cl.
*A61F 9/007*    (2006.01)

(52) U.S. Cl.
CPC ...... *A61F 9/00745* (2013.01); *A61F 9/00754* (2013.01)

(58) Field of Classification Search
CPC ............. A61F 9/00745; A61F 9/00754; B25B 13/461; B25B 13/488; B25B 23/1427
See application file for complete search history.

(56) References Cited

U.S. PATENT DOCUMENTS

| | | | |
|---|---|---|---|
| 1,979,460 A * | 11/1934 | Forsberg | B25B 23/16 81/436 |
| D351,095 S | 10/1994 | Casica | |
| 5,511,451 A | 4/1996 | Steen et al. | |
| 8,231,644 B2 | 7/2012 | Onaga | |
| 8,845,541 B2 | 9/2014 | Strunk et al. | |
| 9,023,072 B2 | 5/2015 | Young et al. | |
| 10,195,724 B2 | 2/2019 | Nino et al. | |
| 10,213,270 B2 | 2/2019 | Cutler | |
| 2010/0331897 A1 | 12/2010 | Lindner | |
| 2013/0305889 A1 * | 11/2013 | Nino | A61B 17/8875 81/475 |
| 2014/0123819 A1 * | 5/2014 | Beemer | F16D 7/002 81/476 |
| 2016/0354581 A1 * | 12/2016 | Ivinson | B25B 23/1422 |
| 2017/0156813 A1 * | 6/2017 | Cutler | B25B 23/1427 |

\* cited by examiner

*Primary Examiner* — Ashley L Fishback
*Assistant Examiner* — Chima U Igboko (57) ABSTRACT

A wrench assembly for attachment and removal of a tip to a handpiece of a surgical system includes a core and a shell including a central portion that defines a central bore. In various embodiments, the core includes an outer portion fixedly coupled to the shell and an inner portion configured for insertion into the central bore. The inner portion is removably coupled to the outer portion by a separation mechanism configured to facilitate separation of the inner portion from the outer portion at a predetermined torque.

13 Claims, 9 Drawing Sheets

APPARATUS AND SYSTEM FOR A DISPOSABLE TORQUE LIMITING TIP WRENCH

BACKGROUND

Field of Technology

The present disclosure relates generally to phacoemulsification surgical systems. In particular, the present disclosure relates to phacoemulsification systems including a disposable torque limiting tip wrench for coupling a tip to a handpiece.

Description of the Background

Cataracts affect more than 22 million Americans age 40 and older, and as the U.S. population ages, more than 53 million Americans are expected to have cataracts by the year 2030. Cataract surgery entails the removal of a lens of an eye that has developed clouding of the eye's natural lens, or opacification. As a result of opacification, light is unable to travel to the retina, thereby causing vision loss. Once vision becomes seriously impaired, cataract surgery is a viable option with a high level of success. During cataract surgery, a surgeon replaces the clouded lens with an intraocular lens (IOL).

Certain surgical procedures, such as phacoemulsification surgery, have been successfully employed in the treatment of certain ocular problems, such as cataracts. Phacoemulsification surgery utilizes a small corneal incision to insert the tip of at least one phacoemulsification handheld surgical implement, or handpiece, through the corneal incision. The handpiece includes a needle which is ultrasonically driven once placed within the incision to emulsify the eye lens, or to break the cataract into small pieces. The broken cataract pieces or emulsified eye lens may subsequently be removed using the same handpiece, or another handpiece, in a controlled manner. The surgeon may then insert a lens implant into the eye through the incision. The incision is allowed to heal, and the result for the patient is typically significantly improved eyesight.

Currently during cataract surgery, the tip for phacoemulsification must be screwed on to the handpiece before the start of every surgery and then unscrewed after the surgery is concluded. This task is currently performed with a tip wrench. There are generally two types of tip wrenches that are used: disposable and reusable. Reusable tip wrenches are made from metal and require sterilization in an autoclave after each use. Disposable tip wrenches are made from plastic but are easily stripped during tightening of the tip onto the handpiece, so much so that a second tip wrench may be required to remove the tip from the handpiece post-surgery.

A problem common to both reusable and disposable tip wrenches is over-torquing. Applying too much torque with a plastic disposable tip wrench may cause the threads of the tip wrench to strip, rendering it unusable. Similarly, over-torquing a reusable tip wrench can over-tighten the tip and thus make removal difficult after the surgery is completed, or possibly damaging the handpiece.

Similarly, if the tip is not secured to the handpiece tightly enough, it can affect ultrasound performance. Specifically, variations in tightness can impact tuning of the handpiece during surgery. A tip wrench that applies consistent torque to the tip during attachment would allow for consistent tuning and performance of the handpiece and also reduce the risks of stripping the tip wrench.

SUMMARY

Various embodiments recite a wrench assembly for attachment and removal of a tip to a handpiece of a surgical system. In various embodiments, the wrench assembly includes a core and a shell including a central portion that defines a central bore. In various embodiments, the core includes an outer portion fixedly coupled to the shell and an inner portion configured for insertion into the central bore, wherein the inner portion is removably coupled to the outer portion by a separation mechanism configured to facilitate separation of the inner portion from the outer portion at a predetermined torque.

Various embodiments further recite a method of assembling and operating a wrench assembly for use in a surgical system that includes a tip and a handpiece. In various embodiments, the method includes inserting an inner portion of a core of the wrench assembly into a central bore of a shell of the wrench assembly. The method also includes attaching an outer portion of the core to an end surface of the shell and inserting the tip into an inner bore of the inner portion. The method further includes rotating the shell and core together in a first direction to a predetermined torque to attach the tip to the handpiece. A separation mechanism of the core causes separation of the inner portion from the outer portion at the predetermined torque.

DESCRIPTION OF THE DRAWINGS

The accompanying drawings are included to provide a further understanding of the invention and are incorporated in and constitute a part of this specification. The drawings illustrate disclosed embodiments and/or aspects and, together with the description, serve to explain the principles of the invention, the scope of which is determined by the claims.

This disclosure is illustrated by way of example and not by way of limitation in the accompanying figure(s). The figure(s) may, alone or in combination, illustrate one or more embodiments of the disclosure. Elements illustrated in the figure(s) are not necessarily drawn to scale. Reference labels may be repeated among the figures to indicate corresponding or analogous elements.

DETAILED DESCRIPTION

It is to be understood that the figures and descriptions of the present disclosure have been simplified to illustrate elements that are relevant for a clear understanding of the present invention, while eliminating, for the purpose of clarity, many other elements found in typical surgical, and particularly optical surgical, apparatuses, systems, and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

Embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that exemplary embodiments may be embodied in different forms. As such, the exemplary embodiments should not be construed to limit the scope of the disclosure. As referenced above, in some exemplary embodiments, well-known processes, well-known device structures, and well-known technologies may not be described in detail.

Figure 1A:
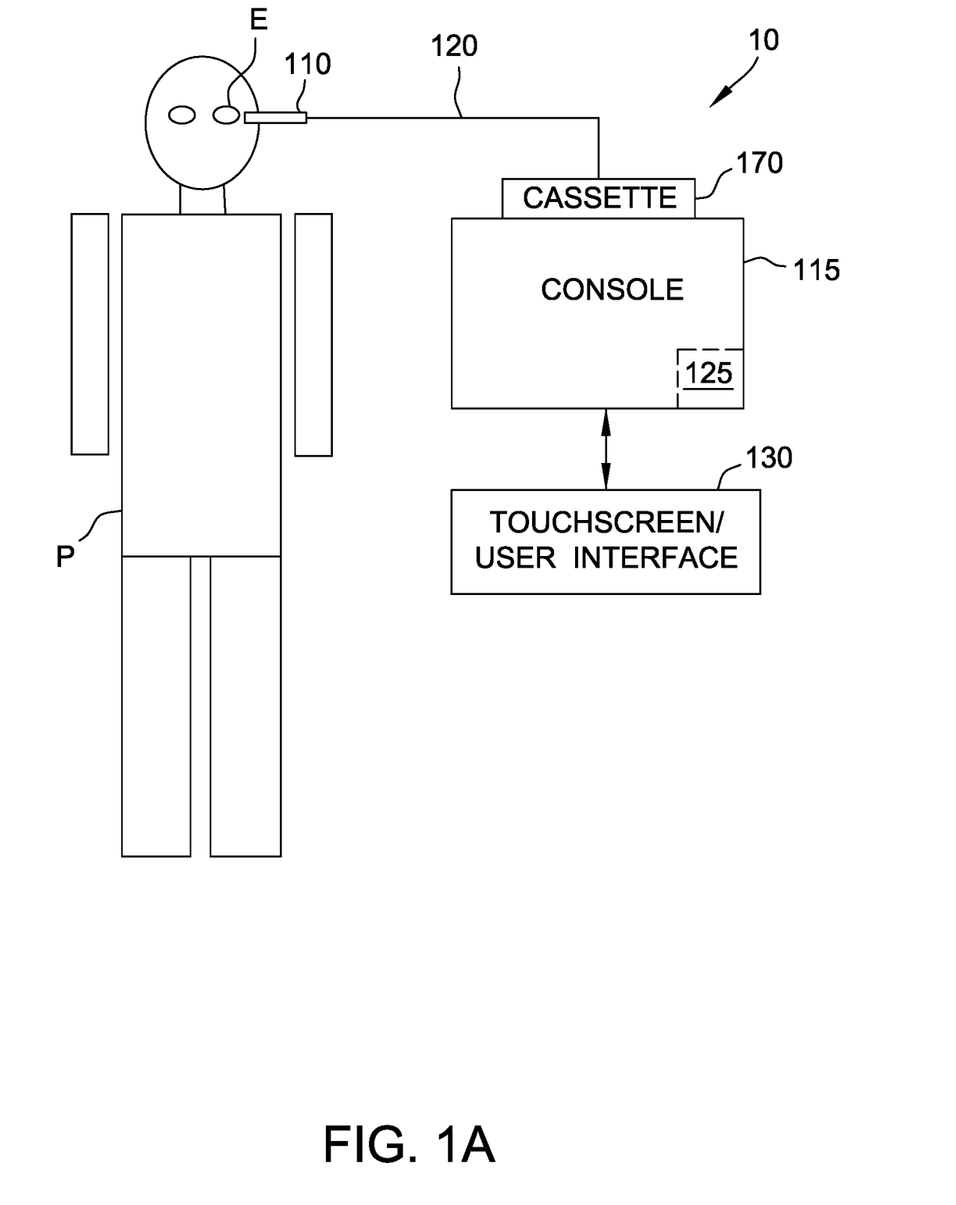
FIG. 1A is a schematic illustrating an eye treatment system in which a cassette is coupled to an eye treatment probe with an eye treatment console under one embodiment.

Referring now to FIG. 1A, an eye treatment system 10 for treating an eye E of a patient P generally includes an eye treatment probe handpiece 110 coupled with a console 115 by a cassette 170. Handpiece 110 generally includes a handle for manually manipulating and supporting an insertable probe tip. The probe tip has a distal end which is insertable into the eye, with one or more lumens in the probe tip allowing irrigation fluid to flow from console 115 and/or cassette 170 into the eye. Aspiration fluid may also be withdrawn through a lumen of the probe tip, with console 115 and cassette 170 generally including a vacuum aspiration source, a positive displacement aspiration pump, or both to help withdraw and control a flow of surgical fluids into and out of eye E. As the surgical fluids may include biological materials that should not be transferred between patients, cassette 170 will often comprise a sterilizable (or alternatively, disposable) structure, with the surgical fluids being transmitted through flexible conduits 120 of cassette 170 that avoid direct contact in between those fluids and the components of console 115.

When a distal end of the probe tip of handpiece 110 is inserted into an eye E, for example, for removal of a lens of a patient P with cataracts, an electrical conductor and/or pneumatic line (not shown) may supply energy from console 115 to an ultrasound transmitter of handpiece 110, a cutter mechanism, or the like. Alternatively, handpiece 110 may be configured as an irrigation/aspiration (I/A) and/or vitrectomy handpiece. Also, the ultrasonic transmitter may be replaced by other means for emulsifying a lens, such as a high energy laser beam. The ultrasonic energy from handpiece 110 helps to fragment the tissue of the lens, which can then be drawn into a port of the tip by aspiration flow. So as to balance the volume of material removed by the aspiration flow, an irrigation flow through handpiece 110 (or a separate probe structure) may also be provided, with both the aspiration and irrigation flows being controlled by console 115.

To avoid cross-contamination between patients without incurring excessive expenditures for each procedure, cassette 170 and its flexible conduits 120 may be disposable. However, the flexible conduit or tubing may be disposable, with the cassette body and/or other structures of the cassette being sterilizable. Cassette 170 may be configured to interface with reusable components of console 115, including, but not limited to, peristaltic pump rollers, a Venturi or other vacuum source, a controller 125, and/or the like.

Console 115 may include controller 125, which may include an embedded microcontroller and/or many of the components common to a personal computer, such as a processor, data bus, a memory, input and/or output devices (including a user interface 130 (e.g. touch screen, graphical user interface (GUI), etc.), and the like. Controller 125 will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 125 may have (or be coupled with) a recording media reader, or the code may be transmitted to controller 125 by a network connection such as an internet, an intranet, an ethernet, a wireless network, or the like. Along with programming code, controller 125 may include stored data for implementing the methods described herein and may generate and/or store data that records parameters corresponding to the treatment of one or more patients.

Figure 1B:
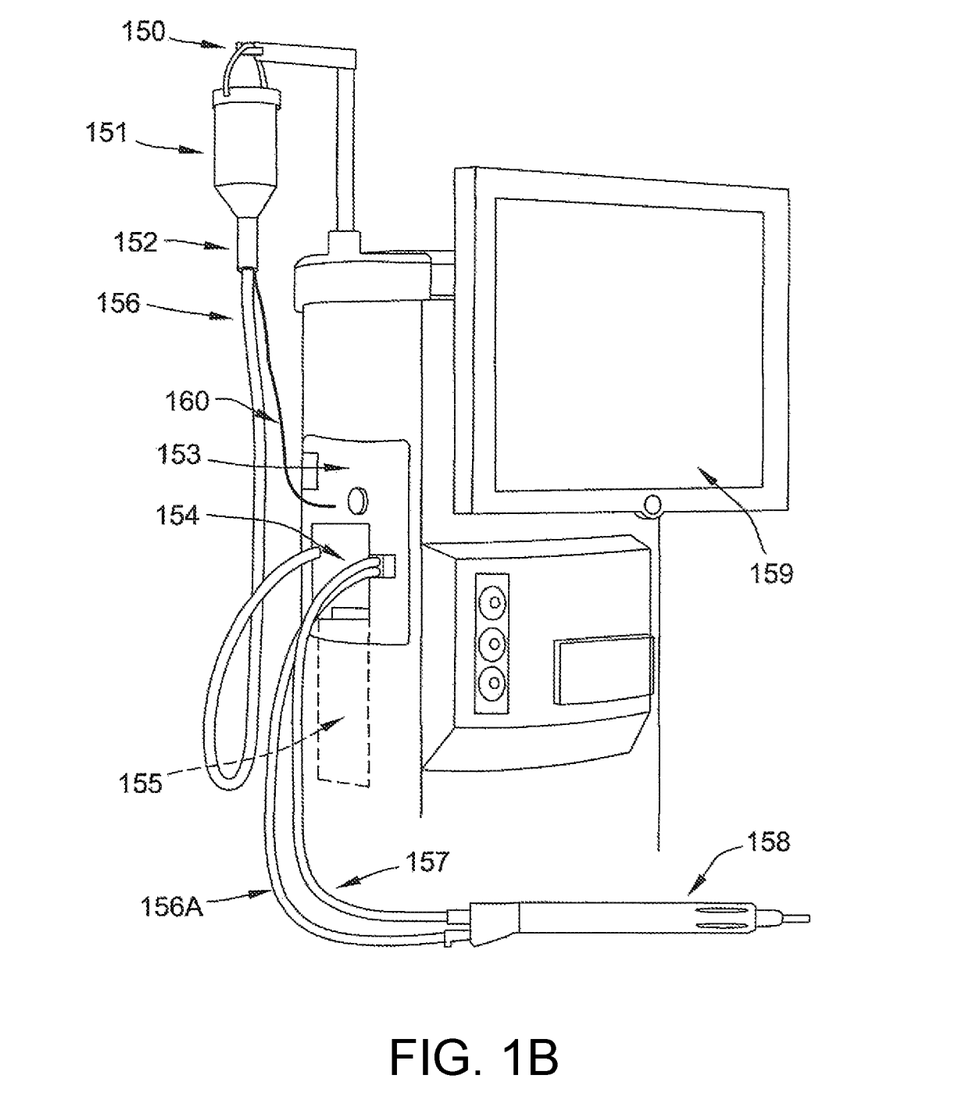
FIG. 1B is a schematic illustrating a surgical eye treatment console under another exemplary embodiment.

Referring now to FIG. 1B, a simplified surgical console is illustrated, where a fluid path may be demonstrated under an exemplary embodiment. In this example, an irrigation source 151 may be configured as a bottle or bag hanging from an IV pole hanger 150. It is understood by those skilled in the art that, while an integrated IV pole is illustrated, other configurations, utilizing standalone/static IV poles, pressurized infusion sources, and/or other suitable configurations, are contemplated by the present disclosure.

An exemplary irrigation path for fluid may be realized via tubing cassette 154 coupled with cassette tubing interface 153, which receives fluid from irrigation source 151 via drip chamber 152. Irrigation line 156A and aspiration line 157 are coupled to handpiece 158. Irrigation fluid may flow from drip chamber 152 through the irrigation tubing 156 into tubing cassette 154. Irrigation fluid may then flow from the tubing cassette through handpiece irrigation line 156A which may be coupled to an irrigation port on handpiece 158. Aspirated fluid may flow from the eye through the handpiece aspiration line 157 back to tubing cassette 154 and into a waste collection bag 155. A touch screen display 159 may be provided to display system operation conditions and parameters, and may include a user interface (e.g., touch screen, keyboard, track ball, mouse, etc.—see controller 125 of FIG. 1A) for entering data and/or instructions to the system of FIG. 1B.

Figure 2:
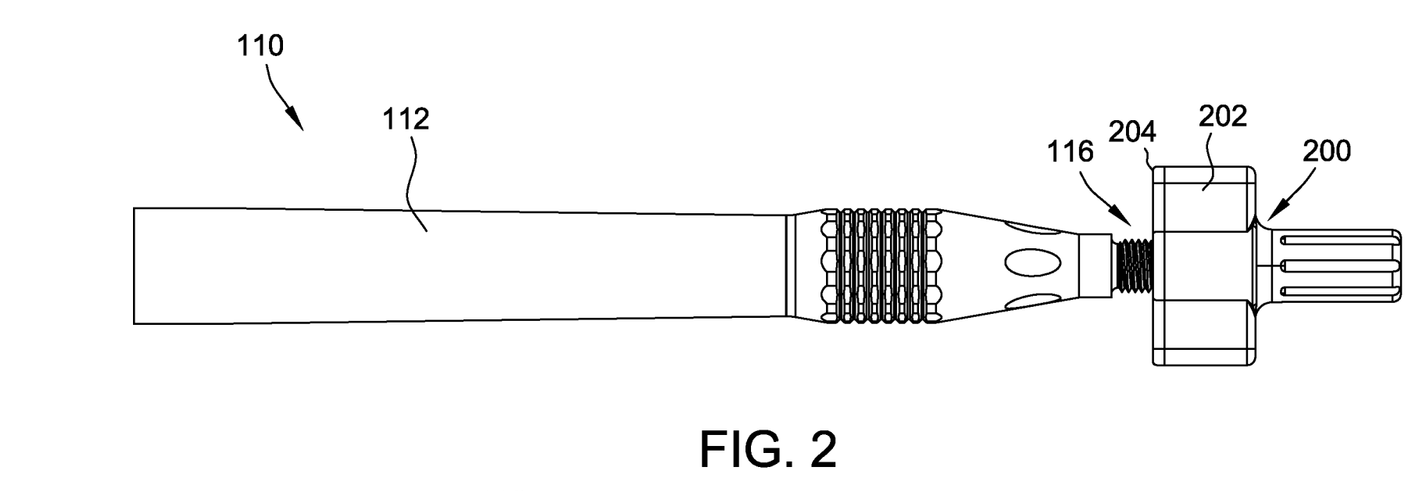
FIG. 2 is a side view of a handpiece for use in the eye treatment system of FIG. 1A, including a wrench assembly.
Figure 3:
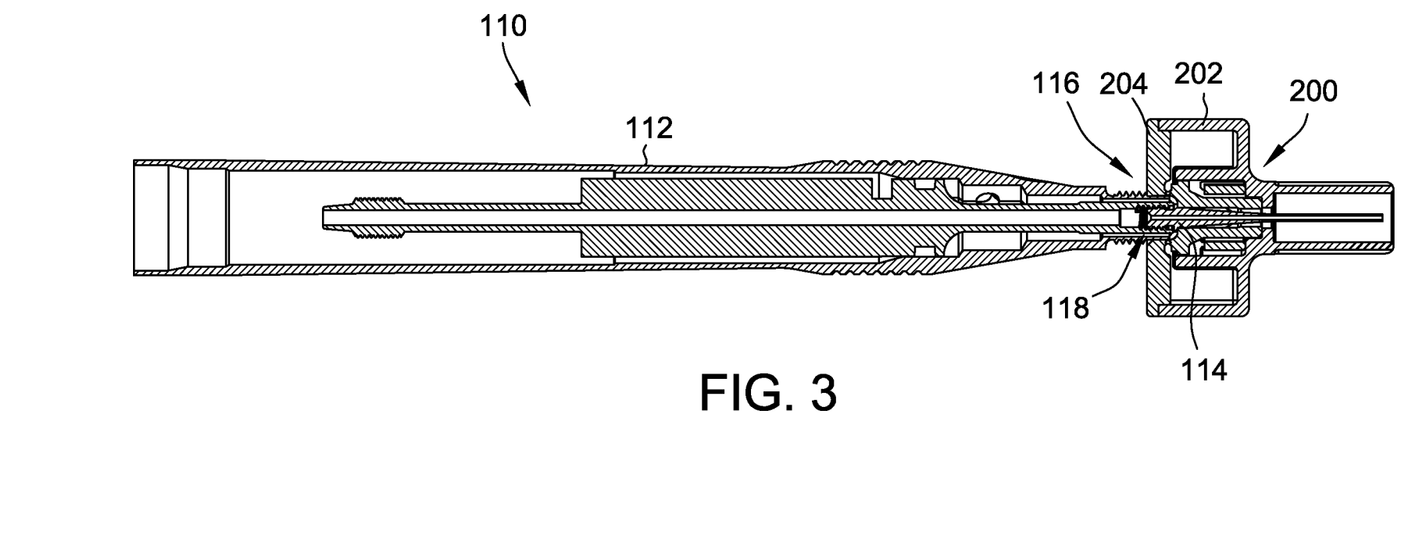
FIG. 3 is a cross-sectional view of the handpiece and wrench assembly shown in FIG. 2.

FIG. 2 is a side view of handpiece 110 for use in the eye treatment system 10 of FIG. 1A and an exemplary wrench assembly 200 attached thereto. FIG. 3 is a cross-sectional view of handpiece 110 and wrench assembly 200. Handpiece 110 generally includes a handle 112 for manually manipulating and supporting an insertable probe tip 114. Probe tip 114 has a distal end which is insertable into the eye, with one or more lumens in the probe tip allowing irrigation fluid to flow from console 115 and/or cassette 170 into the eye. Handle 112 includes a distal end 116 that defines a threaded handle bore 118 into which wrench assembly 200 is configured to rotate tip 114. As described in further detail herein, wrench assembly 200 includes a shell 202 and a core 204 configured to be at least partially inserted into shell 202. Tip 114 extends into wrench assembly 200 and is rotated by wrench assembly 200 to both attach and remove tip 114 from handle 112. Tip 114 may be any tip known in the prior used in conjunction with a handpiece, e.g. phacoemulsification handpiece, irrigation/aspiration handpiece, or the like.

Figure 4:
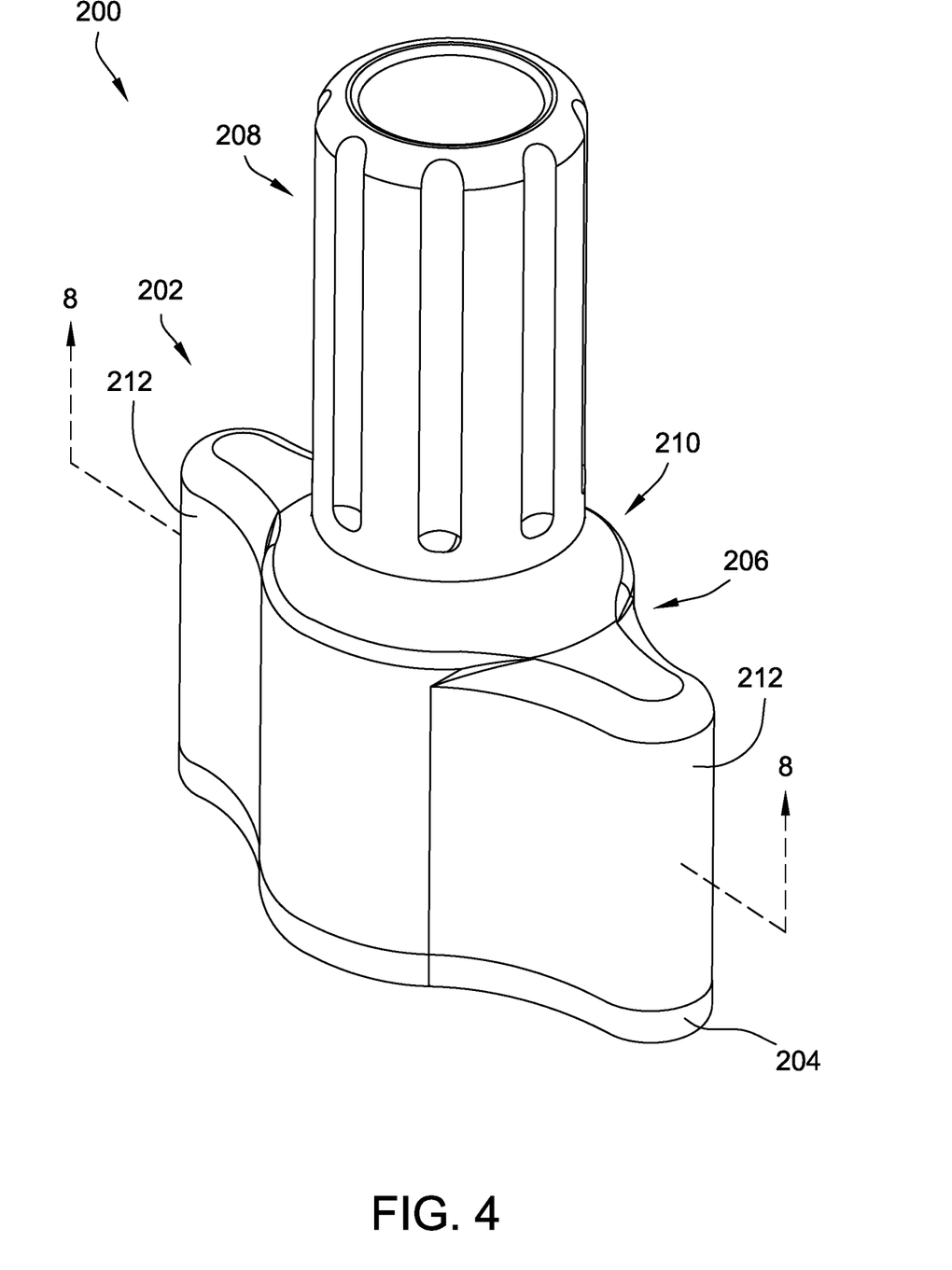
FIG. 4 is a perspective view of the wrench assembly shown in FIG. 2.
Figure 5:
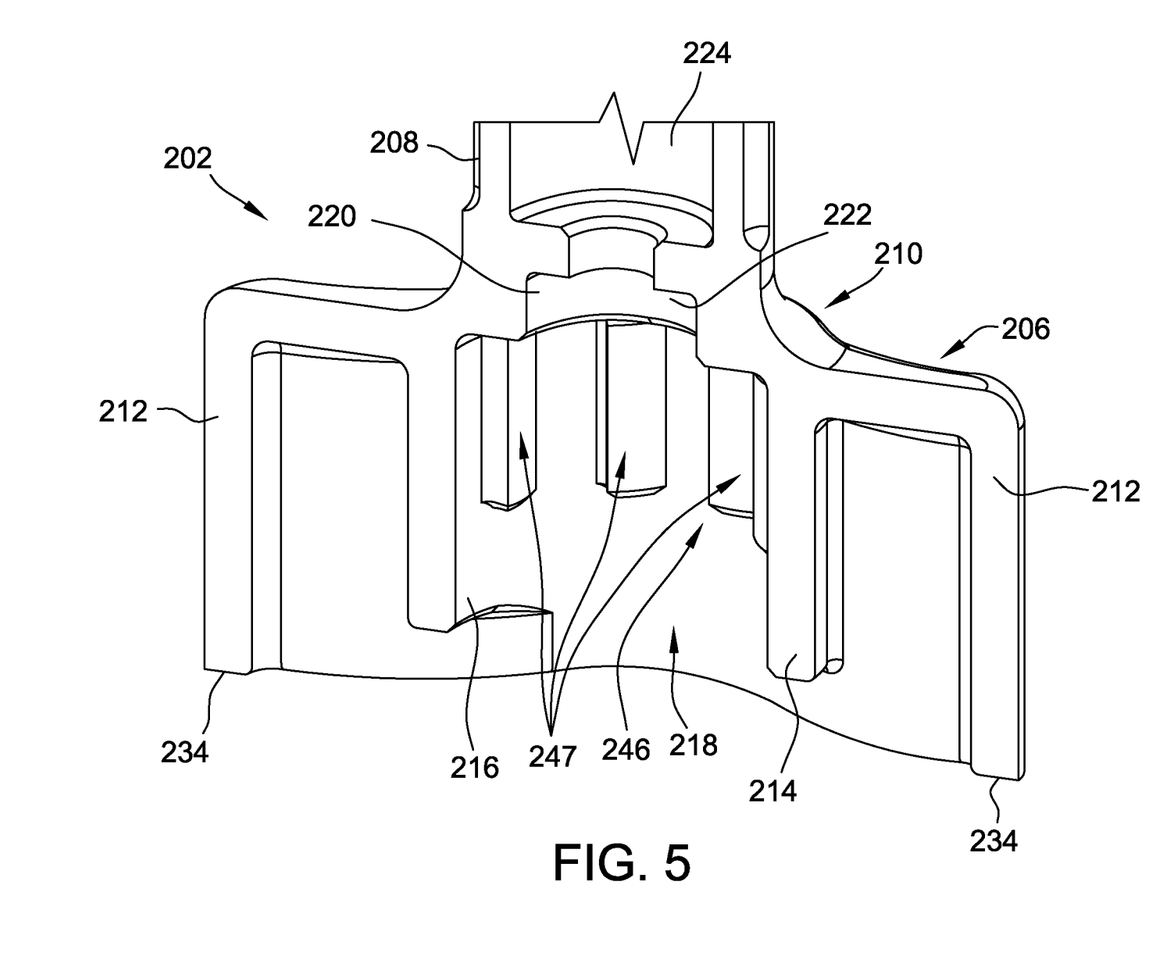
FIG. 5 is a cross-sectional perspective view of a shell portion of the wrench assembly shown in FIG. 4.
Figure 6:
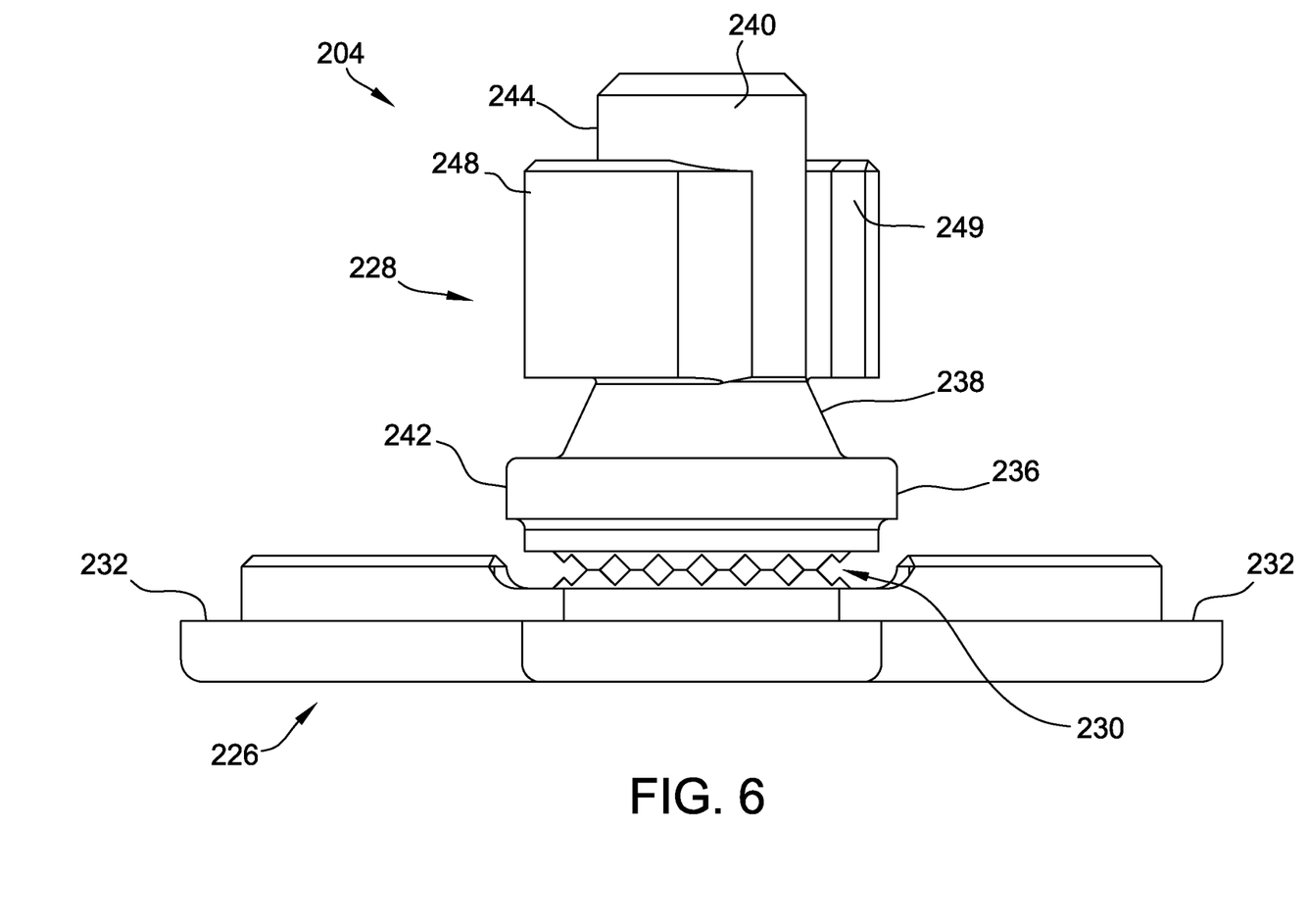
FIG. 6 is a side view of a core portion of the wrench assembly shown in FIG. 4.
Figure 7:
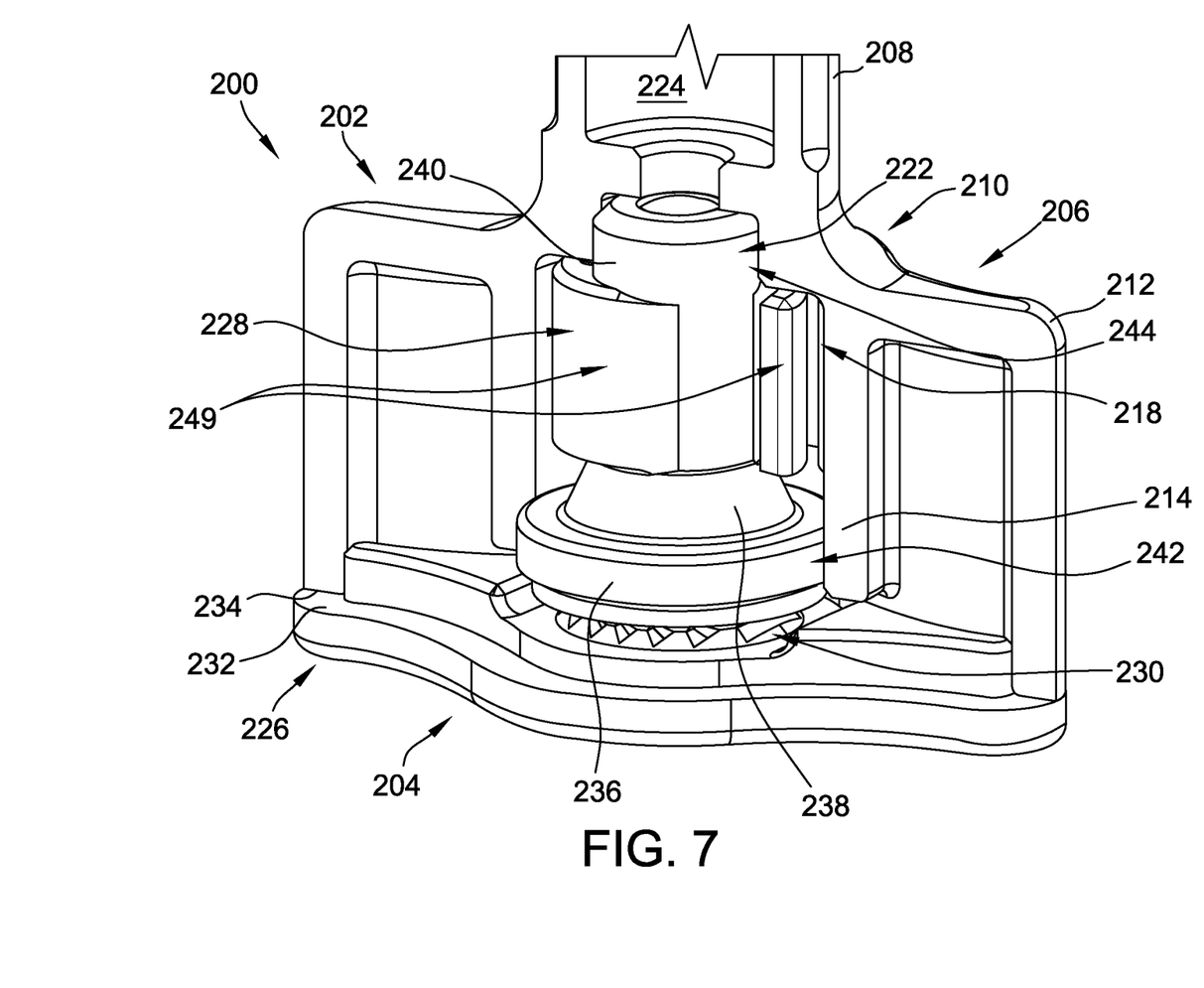
FIG. 7 is a cross-sectional perspective view of the shell portion illustrating the core portion positioned therein.
Figure 8:
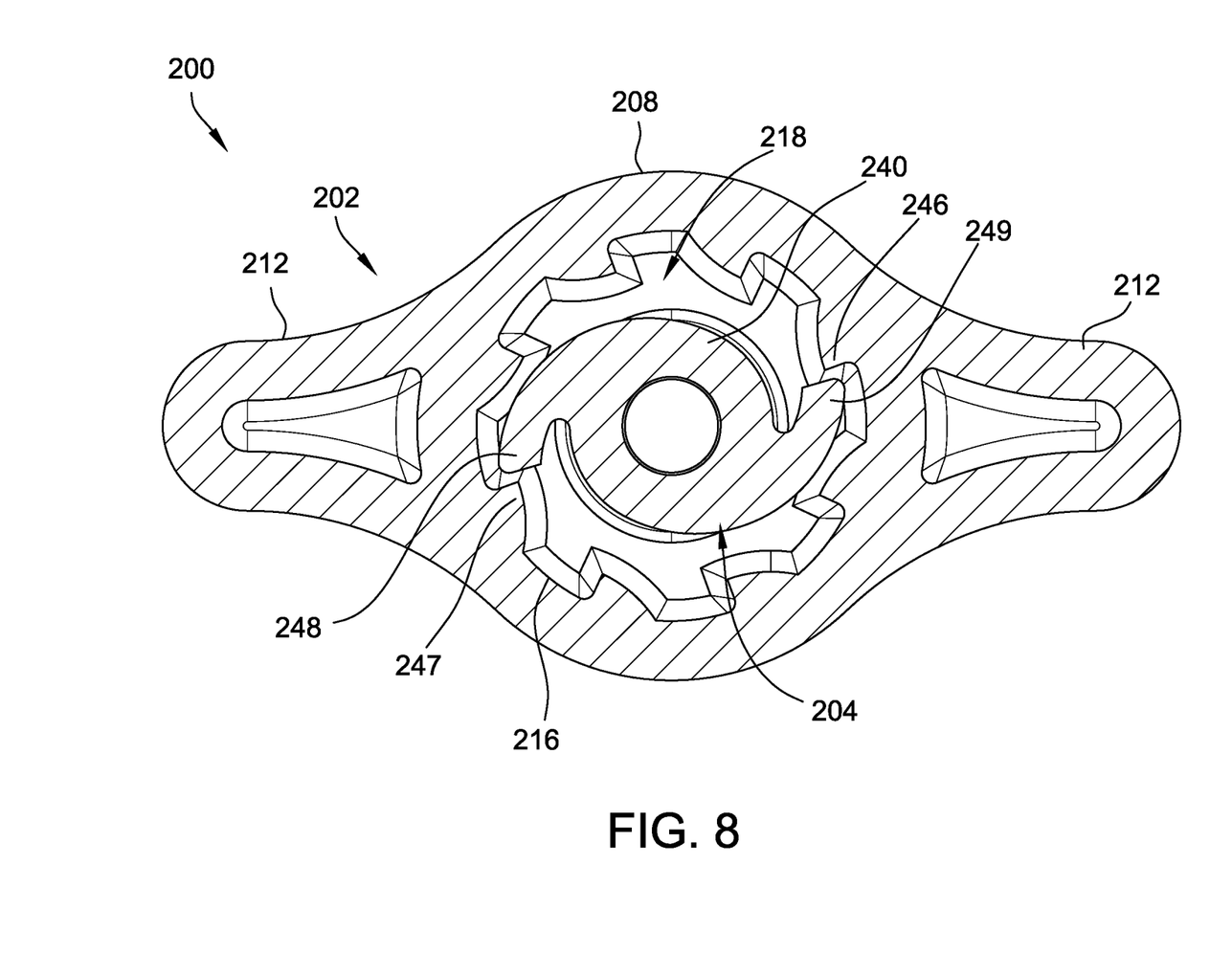
FIG. 8 is a cross-sectional bottom view of the wrench assembly taken along line 8-8 shown in FIG. 4.

FIG. 4 is a perspective view of the wrench assembly 200. FIG. 5 is a cross-sectional perspective view of shell 202 of wrench assembly 200. FIG. 6 is a side view of core 204 of wrench assembly 200. FIG. 7 is a cross-sectional perspective view of shell 202 illustrating core 204 positioned therein, and FIG. 8 is a cross-sectional bottom view of wrench assembly 200 taken along line 8-8 shown in FIG. 4.

In the exemplary embodiment, wrench assembly 200 includes shell 202 having a base portion 206 and an extension portion 208 that extends away from base portion 206. Base portion 206 includes an annular central portion 210 and a pair of wings 212 that extend from opposing sides of central portion 210. In one embodiment, extension portion includes knurling to facilitate rotation of wrench assembly 200 by the technician. Similarly, wings 212 extend out from a central axis to provide additional leverage for a technician to facilitate rotation of wrench assembly 200.

As illustrated in FIG. 5, central portion 210 of shell 202 includes an interior annular wall 214 having an inner surface 216 that defines a central bore 218 of shell 202. In one embodiment, as described herein, central bore 218 receives at least a portion of core 204. Central portion 210 also includes a second annular wall 220 that defines a counterbore 222 with central bore 218. Similarly, extension portion 208 includes an extension bore 224 that is aligned with counterbore 222 and central bore 218 such that tip 114 extends through bores 218, 222, and 224 when positioned within shell 202.

Referring now to FIG. 6 with a view to FIG. 7, core 204 includes an outer portion 226 coupled to shell 202 and an inner portion 228 configured for insertion into central bore 218. In the exemplary embodiment, inner portion 228 is removably coupled to outer portion by a separation mechanism 230. In one embodiment, separation mechanism 230 includes at least one of a plurality of perforations and circumferential groove in core 204. Separation mechanism 230 facilitates separation of inner portion 228 from outer portion 226 at a predetermined torque, as described in detail herein. Outer portion 226 includes a core end surface 232 that is configured to be bonded (e.g. in an embodiment, permanently) to a shell end surface 234 (shown in FIG. 5). In one embodiment, end surfaces 232 and 234 are ultrasonically welded together. In another embodiment, end surfaces 232 and 234 are adhesively bonded. Generally, end surfaces 232 and 234 are coupled together in any manner that restricts or prevent relative movement between outer portion 226 and shell 202.

Inner portion 228 includes a flange 236, an intermediate portion 238 extending away from flange 236, and an extension portion 240 extending from intermediate portion 238. In the exemplary embodiment, flange 236 includes a first bearing surface 242 configured to engage inner surface 216 of annular wall 214. Similarly, extension portion 240 includes a second bearing surface 244 configured to engage second annular wall 220. Bearing surfaces 242 and 244 are spaced apart on inner portion 228 to facilitate alignment of inner portion 228 with shell 202.

As shown in FIGS. 5-8, shell 202 includes a first rotation mechanism 246 and core 204 includes a second rotation mechanism 248 configured to selectively engage first rotation mechanism 246. Specifically, first rotation mechanism 246 extends inwards into central bore 218 from inner surface 216 of annular wall 214. Similarly, second rotation mechanism 248 extends outwards from extension portion 240 of core 204 such that second rotation mechanism 248 engages first rotation mechanism 246 when inner portion 228 of core 204 is positioned within central bore 218 of shell 202. In one embodiment, first rotation mechanism 246 includes a plurality of ratchet members 247, and second rotation mechanism 248 includes at least one pawl 249. In other embodiments, first rotation mechanism 246 includes at least one pawl 249, and second rotation mechanism includes a plurality of ratchet members 247. As described in further detail herein, pawls 249 are flexible such that when shell 202 rotates in a first direction around inner portion 228, pawls 249 are biased inward and do not engage ratchet members 247. In such a configuration, inner portion 228 remains stationary within central bore 218 as shell 202 rotates around it. However, when shell 202 is rotated in the opposite direction, ratchet members 247 engage pawls 249 and rotate inner portion 228 of core 204 therewith.

Figure 9:
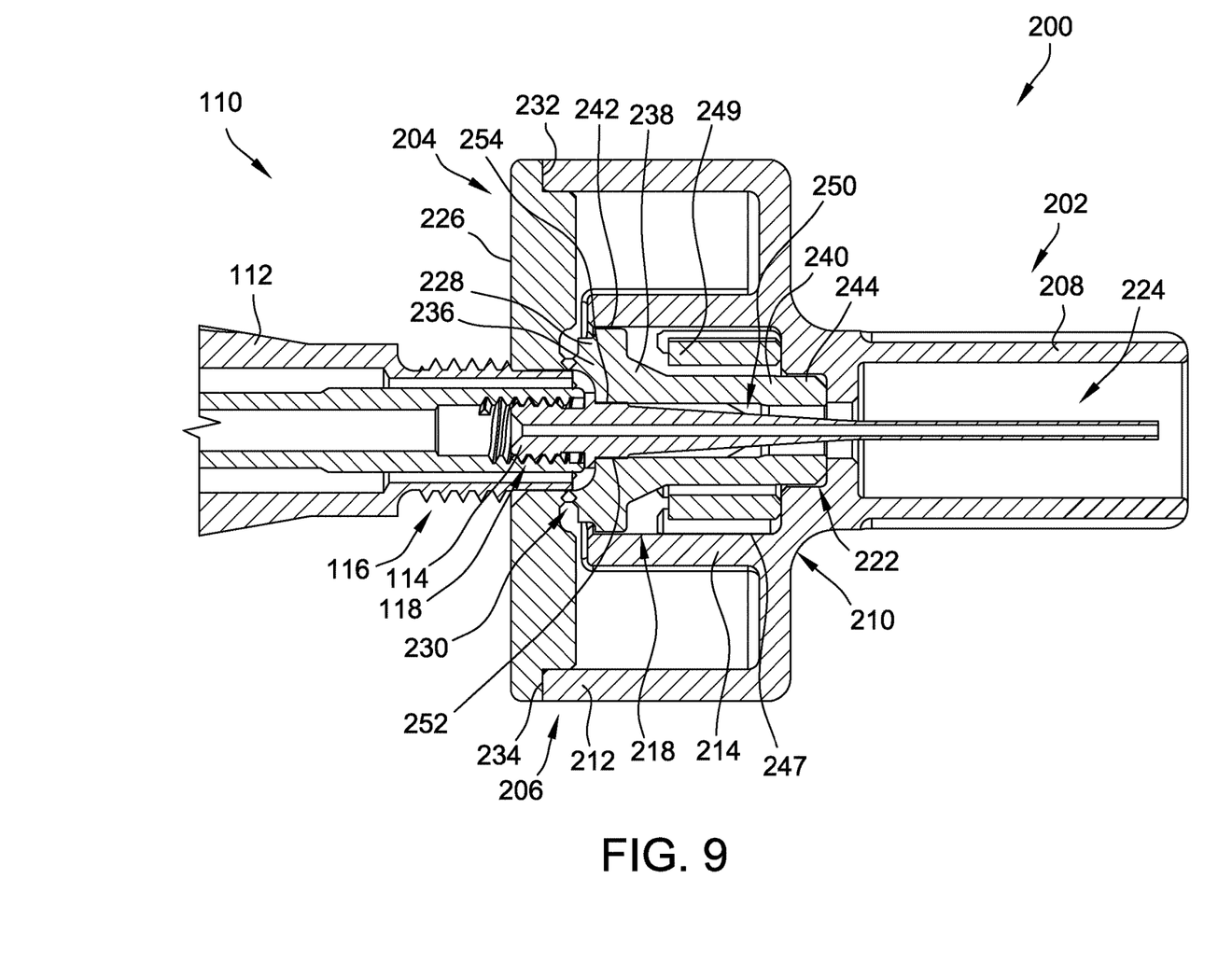
FIG. 9 is an enlarged cross-sectional view of the handpiece and wrench assembly shown in FIG. 3.

FIG. 9 is an enlarged cross-sectional view of the handpiece and wrench assembly shown in FIG. 3. In the exemplary embodiment, wrench assembly 200 is made from a plastic material such that wrench assembly can be produced at less expense to allow for disposal of wrench assembly 200 after a single use. In other embodiments, wrench assembly 200 is made from other materials, such as, but not limited to metal.

In operation of wrench assembly 200 in eye treatment system 10, core 204 is inserted into shell 202 such that inner portion 228 of core 204 is positioned within central bore 218 of shell 202. In such a configuration, a core bore 250 of inner portion 228 is aligned with bores 218, 222, and 224 of shell 202. In various embodiments, outer portion 226 of core 204 is attached to shell 202 by affixing core end surface 232 to shell end surface 234. As described herein, in one embodiment, surfaces 232 and 234 are attached using ultrasonic welding, press fitting, an adhesive, or a combination thereof. In other embodiments, surfaces 232 and 234 are attached by any means that facilitates operation of wrench assembly 200 as described herein. Tip 114 may then be inserted into core bore 250 such that a mating surface 252 of tip 114 engages a receiving surface 254 of inner portion 228. Surfaces 252 and 254 are configured such that receiving surface 254 prevents rotation of tip 114 relative to inner portion 228. More specifically, surfaces 252 and 254 allow tip 114 to couple to inner portion 228 such that wrench assembly 200 rotates tip 114 into distal end of handle 112. In one embodiment, mating surface 252 and receiving surface 254 are correspondingly rectangular in shape. In various embodiments, surfaces 252 and 254 are correspondingly pentagon-shaped, hexagon-shaped, star-shaped, or Torx-shaped. Generally, surfaces 252 and 254 have any corresponding shape that enables operation as described herein.

In various embodiments, once tip 114 is coupled with wrench assembly 200, wrench assembly 200 is attached to handpiece 110 by inserting distal end 116 of handle 112 into wrench assembly 200 to align tip 114 with handle bore 118. Tip 114 is attached to handpiece 110 by rotating shell 202 and core 204 together in a first direction to a predetermined torque. As described herein, at the predetermined torque, separation mechanism 230 facilitates separation of inner portion 228 from outer portion 226. Specifically, separation mechanism 230 includes lines of weakness, such as, but not limited to, a plurality of perforations and/or a circumferential groove around core 204 that are design to break at a predetermined torque. Torque is applied by rotating shell 202 and threading tip 114 into handle bore 118. The further tip 114 is threaded into handle bore 118, the more torque required for further insertion of tip 114. To prevent over-torquing, which may damage tip 114 and/or handpiece 110 or cause stripping of wrench assembly 200, inner portion 228 is designed to separate from outer portion 226 once the predetermined torque is reached that indicates tip 114 is fully inserted into handle 112. In various embodiments, the predetermined torque is less than 10 inch-pounds (in-lb). Specifically, in some embodiments, the predetermined torque is within a range of between 2 in-lb and 5 in-lb. Generally, the predetermined torque is any torque that enables operation of wrench assembly 200 as described herein.

When the predetermined torque is reached and separation of inner portion 228 from outer portion 226 has occurred, further rotation of shell 202 in the tightening direction causes core rotation mechanism 248, such as pawls 249, to be biased against shell rotation mechanism 246, such as ratchet members 247, such that tip 114 and inner portion 228 remain stationary within central bore 218 of shell 202.

Wrench assembly 200 may then be removed from tip 114 and handpiece 110 and surgery may be performed. To remove tip 114 from handle 112 after surgery, wrench assembly 200 is replaced over tip 114 such that receiving surface 254 engages with mating surface 252. Shell 202 and core 204 are then rotated together in the opposite direction to remove tip 114 from handpiece 110. Specifically, rotating shell 202 in the opposite, loosening direction causes pawls 249 to engage ratchet members 247 such that inner portion 228 rotates with shell 202. Rotation of inner portion 228 causes rotation of tip 114 to facilitate removal. Wrench assembly 200 and tip 114 can then be disposed of.

The implementations described herein relate a wrench assembly for attachment and removal of a tip to a handpiece of a surgical system. In various embodiments, the wrench assembly includes a core and a shell including a central portion that defines a central bore. In various embodiments, the core includes an outer portion fixedly coupled to the shell and an inner portion configured for insertion into the central bore. The inner portion of the core is removably coupled to the outer portion of the core by a separation mechanism configured to facilitate separation of the inner portion from the outer portion at a predetermined torque.

The separation mechanism includes lines of weakness, such as, but not limited to, a plurality of perforations and/or a circumferential groove around the core that is designed to break at the predetermined torque to prevent over-torquing to prevents damage to the tip and/or handpiece. Additionally, the predetermined torque is designed to be less than the torque required to strip the wrench-tip interface, which reduces the risk of stripping the wrench assembly. Furthermore, the predetermined torque means that a consistent amount of torque is applied each time the handpiece is used, which reduces variations in the tightness of the tip and improves the consistency of ultrasonic tuning.

In various embodiments, further rotation of the shell in the tightening direction after separation of the core causes the pawls of the core to be biased against the ratchet members of the shell such that the tip and the inner portion remain stationary within the central bore of the shell. To remove the tip from the handle after surgery, the shell and the core are rotated together in the opposite direction to cause the pawls to engage the ratchet members such that the inner portion rotates with the shell. Rotation of the inner portion causes rotation of the tip to facilitate removal.

Those of skill in the art will appreciate that the herein described apparatuses, devices, systems and methods are susceptible to various modifications and alternative constructions. There is no intention to limit the scope of the invention to the specific constructions described herein. Rather, the herein described systems and methods are intended to cover all modifications, alternative constructions, and equivalents falling within the scope and spirit of the disclosure, any appended claims and any equivalents thereto.

In the foregoing detailed description, it may be that various features are grouped together in individual embodiments for the purpose of brevity in the disclosure. This method of disclosure is not to be interpreted as reflecting an intention that any subsequently claimed embodiments require more features than are expressly recited.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather are to be accorded the widest scope consistent with the principles and novel features disclosed herein.

What is claimed is:

1. A wrench assembly for attachment and removal of a threaded tip to a handpiece of a surgical system, the wrench assembly comprising:
    a shell comprising a central portion having a first diameter and an extension portion that extends axially away from the central portion and having a second diameter, the central portion and extension portion defining a central bore, wherein the central portion includes a pair of oppositely disposed wings extending outwardly from an axis of the central bore, the pair of oppositely disposed wings configured to provide leverage to facilitate rotation of the wrench assembly; and
    a core disposed within the central bore of the shell and adapted to receive and engage a mating surface of the threaded tip for attachment and removal of the threaded tip with corresponding threads of the handpiece, the core comprising:
        an outer portion fixedly coupled to the central bore of the shell; and
        an inner portion having an inner bore including a tip receiving surface configured to receive and engage the mating surface of the threaded tip, wherein the inner portion is removably coupled to an inner surface of the outer portion by a separation mechanism configured to facilitate separation of the inner portion from the outer portion at a predetermined torque when rotating the wrench assembly to attach the threaded tip to the handpiece.

2. The wrench assembly of claim 1, wherein the predetermined torque is less than 10 inch-pounds (in-lb).

3. The wrench assembly of claim 2, wherein the predetermined torque is within a range of between 2 in-lb and 5 in-lb.

4. The wrench assembly of claim 1, wherein the shell and the core are formed from plastic.

5. The wrench assembly of claim 1, wherein the central portion comprises an interior annular wall that defines the central bore, wherein the interior annular wall comprises a first rotation mechanism extending into the central bore.

6. The wrench assembly of claim 5, wherein the inner portion of the core comprises a second rotation mechanism configured to selectively engage the first rotation mechanism.

7. The wrench assembly of claim 6, wherein the first rotation mechanism comprises a plurality of ratchet members, and wherein the second rotation mechanism comprises at least one pawl.

8. The wrench assembly of claim 1, wherein the separation mechanism comprises at least one of a circumferential groove and a plurality of perforations.

9. The wrench assembly of claim 1, wherein the central portion comprises a first annular wall and a second annular wall, wherein the second annular wall-defines a counterbore with the central bore, and wherein the core comprises a first bearing surface configured to contact the first annular wall and a second bearing surface configured to contact the second annular wall.

10. The wrench assembly of claim 1, wherein the inner portion of the core comprises:
a flange comprising a first bearing surface configured to engage the central portion of the shell;
an intermediate portion extending from the flange in a direction opposite the outer portion; and
an extension portion extending from the intermediate portion, wherein the extension portion comprises a second bearing surface configured to engage the central portion of the shell.

11. The wrench assembly of claim 1 wherein the extension portion includes knurling to facilitate rotation of the wrench assembly.

12. The wrench assembly of claim 1 wherein the tip receiving surface configured to receive and engage the mating surface of the threaded tip comprises a shape of one of a rectangle, a pentagon, a hexagon, a star or a torx.

13. The wrench assembly of claim 1 wherein the second diameter is smaller than the first diameter.

* * * * *